United States Patent [19]

Mason

[11] Patent Number: 5,251,651
[45] Date of Patent: Oct. 12, 1993

[54] WATERPROOF DENTAL FLOSSING TOOL

[76] Inventor: Robert F. Mason, 10763 Hedda Pl., Cerritus, Calif. 90701

[21] Appl. No.: 819,861

[22] Filed: Jan. 13, 1992

Related U.S. Application Data

[63] Continuation-in-part of Ser. No. 504,003, Apr. 4, 1990, abandoned.

[51] Int. Cl.⁵ .............................................. A61C 15/00
[52] U.S. Cl. ................................... 132/326; 132/325; 132/324
[58] Field of Search ............... 132/323, 324, 325, 326, 132/327

[56] References Cited

U.S. PATENT DOCUMENTS

| | | | |
|---|---|---|---|
| 1,608,212 | 11/1926 | Hochstadter | 132/326 |
| 1,990,404 | 2/1935 | Doner | 132/326 |
| 3,830,247 | 8/1974 | Kaphalakos | 132/325 X |
| 4,214,598 | 7/1980 | Lee | 132/325 |

*Primary Examiner*—John J. Wilson
*Assistant Examiner*—Jeffrey A. Smith
*Attorney, Agent, or Firm*—Robert M. Sperry

[57] ABSTRACT

An improved dental flossing tool having a clamp (clamping means) located adjacent the tip where the flossing material exits the tool serving to clamp the flossing material to prevent entry of moisture through the tip, together with a water-impervious seal (means) for manually controlling withdrawal of the flossing material from the storage area within the dental flossing tool.

12 Claims, 2 Drawing Sheets

WATERPROOF DENTAL FLOSSING TOOL

RELATED CASES

This application is a continuation-in-part of my co-pending patent application Ser. No. 504,003, filed Apr. 4, 1990, and now abandoned.

FIELD OF INVENTION

This invention relates to dental flossing tools and is particularly directed to waterproof dental flossing tools.

PRIOR ART

As is well known, the flossing of teeth is a very important part of proper dental hygiene. Unfortunately, many people fail to follow this procedure or perform the flossing operation incorrectly or inefficiently. Numerous types of dental flossing tools have been proposed heretofore to overcome these problems. One major problem that has been encountered in the use of dental floss is the fact that, despite the fact that dental floss is usually used in proximity to water, it is undesirable for the flossing material to become wet. Unfortunately, dental flossing material is highly absorptive and attracts moisture like a wick. However, air-borne moisture frequently carries germs, bacteria, etc. and, especially if the flossing material is stored in a dark area having poor air circulation, such as the interior of many prior art flossing tools, this provides an ideal environment for growth and development of such contaminants. Obviously, this situation is undesirable and may even be dangerous to the user. Thus, none of the prior art dental flossing tools has been entirely satisfactory.

BRIEF SUMMARY AND OBJECTS OF THE INVENTION

These disadvantages of prior art dental flossing tools are overcome with the present invention and an improved dental flossing tool is provided which positively precludes moisture from entering the tool to reach the floss material storage area. In fact, it has been found that the dental flossing tool of the present invention can be safely used, even while the user is taking a shower, without permitting moisture to enter the dental floss material storage area.

The advantages of the present invention are preferably attained by providing an improved dental flossing tool having clamping means, located adjacent the tip where the flossing material exits the tool, and serving to clamp the flossing material to prevent entry of moisture through the tip, together with water-impervious means for manually controlling withdrawal of the flossing material from the storage area within the dental flossing tool.

Accordingly, it is an object of the present invention to provide an improved dental flossing tool.

Another object of the present invention is to provide an improved dental flossing tool having an internal storage area for flossing material and having means for preventing moisture from entering the interior of the tool to reach the flossing material within the storage area.

A further object of the present invention is to provide an improved dental flossing tool having a tip where flossing material exits the tool and having mean located adjacent the tip for preventing moisture from passing through the tip to the interior of the tool.

Another object of the present invention is to provide an improved dental flossing tool having an internal storage area for dental flossing material, together with water-impervious manual means for controlling withdrawal of the flossing material from the storage area.

A specific object of the present invention is to provide an improved dental flossing tool having clamping means, located adjacent the tip where the flossing material exits the tool, and serving to clamp the flossing material to prevent entry of moisture through the tip, together with water-impervious means for manually controlling withdrawal of the flossing material from the storage area within the dental flossing tool.

These and other objects and features of the present invention will be apparent from the following detailed description, taken with reference to the figures of the accompanying drawing.

DETAILED DESCRIPTION OF THE INVENTION

Figure 1:
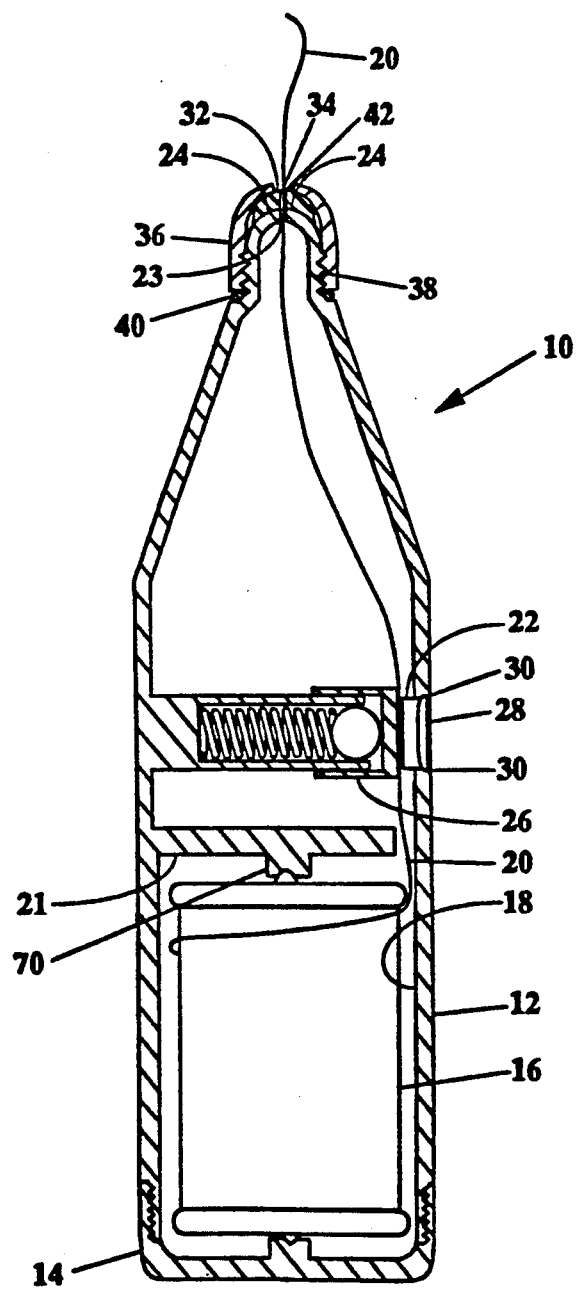
FIG. 1 is a longitudinal section through a dental flossing tool embodying the present invention.

In that form of the present invention chosen for purposes of illustration in FIG. 1, a dental flossing tool, indicated generally at 10, is shown comprising a generally cylindrical, hollow handle 12 having a removable rear end portion 14 to permit a spool 16 of dental flossing material to be loaded into or removed from a storage area 18 within the handle 12. A strand 20 of the flossing material is threaded through an apertured plate 21 and a suitable brake member 22 and out through opening 23 in the tip 24 of the handle 12, where the strand 20 can be grasped by the user to perform the flossing operation. The details of the brake mechanism are shown in my copending patent applications Ser. No. 113,887, filed Oct. 27, 1987, now abandoned, and Ser. No. 478,527, filed Feb. 12, 1990, now abandoned. However, as seen in FIG. 1, the brake member 22 is actuated manually, as by button 26, and a flexible, water-impervious membrane 28 is sealingly mounted in an annular recess 30 to overlie the button 26 and, hence, to permit actuation of the button 26 while precluding entry of moisture about the button 26 into the storage area 18. To further prevent entry of moisture into the interior of the handle 12, an outer tip 32 is provided formed of flexible material, such as rubber and having an axial bore 34 to permit passage therethrough of the strand 20 of flossing material. An outer member 36, formed of rigid material, is provided extending about the outer tip 32 and having threaded connection to the tip 24 of the handle 12, as seen at 38 in FIG. 1, and suitable means, such as O-ring 40 is provided to create a waterproof seal between the outer member 36 and the tip 24 of the handle 12. The outer member 36 is formed with a central opening 42 of greater diameter than the bore 34 of the outer tip 32. When the outer member 36 is threaded more tightly on the tip 24, the edges of the opening 42 of the outer member 36 bear against the flexible outer tip 32, causing the outer tip 32 to clamp against the strand 20 of flossing material and precluding entry on moisture through the bore 34 of outer tip 32 and opening 23 of the tip 24 of handle 12 to the interior of the handle 12. When the outer member 36 is threaded less tightly on the tip 24 of handle 12, the edges of opening 42 of outer member 36 release the outer tip 32 and, hence, release pressure on the strand 20 of flossing material to permit the strand 20 of flossing material to be withdrawn, with more or less friction or drag further, out of the storage area 18 within the handle 12.

In use, a user removes the rear end 14 of the handle 12 and inserts a spool 16 of flossing material into the storage area 18 within the handle 12. Next, the user unthreads outer member 36 sufficiently to permit the strand 20 of flossing material to pass through bore 34 of the flexible outer tip 32. By pressing the button 26, through the water-impervious membrane 28, the user then threads the strand 20 of flossing material through the brake member 22, through opening 23 in the tip 24 of handle 12 and through bore 34 of the flexible outer tip 32. Upon release of the button 26, the brake member 22 serves to prevent further withdrawal of the strand 20 of flossing material from the spool 16 within the storage area 18 of the handle 12. Finally, the user threads the outer member 36 more tightly onto the tip 24 of the handle 12, causing the edges of the opening 42 of the outer member 36 to bear against the flexible outer tip 32 and causing the flexible outer tip 32 to clamp against the strand 20 of flossing material to retard or slow the further withdrawal of the strand 20 from the tip 24 of the handle 12 and to preclude entry of moisture through bore 34 of the outer tip 32 and opening 23 of tip 24 of the handle 12. With the outer member 36 thus causing the outer tip 32 to clamp the strand 20 to preclude entry of moisture through tip 24 of the handle 12, and with the water-impervious membrane 28 precluding entry of moisture about the button 26, moisture is positively prevented from entering into the interior of the handle 12 and, hence, cannot be absorbed by the flossing material on spool 16 within the storage area 18 of the handle 12. Consequently, it is possible to use the dental flossing tool 10 even in a highly humid environment, such as while the user is taking a shower. It has not been possible to provide this measure of moisture protection for the flossing material with the dental flossing tools of the prior art.

Figure 2:
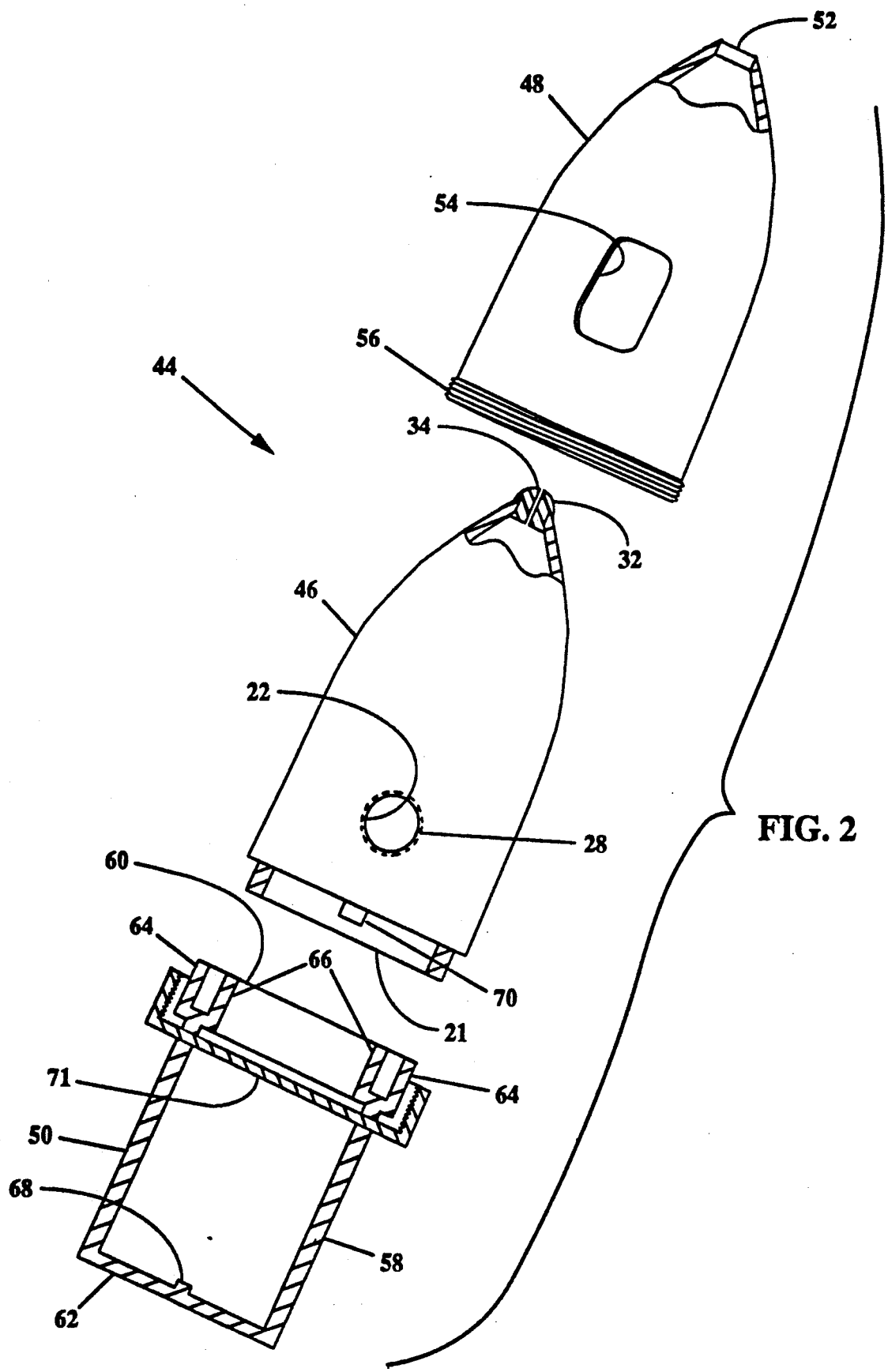
FIG. 2 is an exploded view, partly in section, showing an alternative form of the dental flossing tool of FIG. 1.

In the form of the present invention shown in FIG. 2, a dental flossing tool indicated generally at 44, is shown comprising a tool portion 46, an outer shield 48 and a storage portion 50. The tool portion 46 is substantially identical, internally and externally, to the dental flossing tool 10 of FIG. 1 except that 1) the apertured plate 21 forms the rear end of the tool portion 46 of dental flossing tool 44, and 2) the outer member 36 of the dental flossing tool 10 of FIG. 1 is replaced by the outer shield 48 in the dental flossing tool 44 of FIG. 2. As shown, the tool portion 46 of the dental flossing tool 44 has a flexible outer tip 32 having an axial bore 34 to permit passage therethrough of a strand of flossing material, not shown. The tool portion 46 also has a manually actuable brake button (not shown) located internally of the tool portion 44 adjacent opening 23 and covered by a flexible, water-impervious membrane 28. The outer shield 48 of the dental flossing tool 44 is formed to encircle the tool portion 46 and extends approximately the full length of the tool portion 46, but is not attached to the tool portion 46. The outer shield 48 has a first opening 52 formed adjacent the forward end thereof which serves to bear against the flexible outer tip 32 of the tool portion 46, as described hereafter. The outer shield 48 also has a second opening 54 formed in the side wall thereof to provide access to the manually actuated brake button located within the tool portion 46 adjacent opening 22. Also, the rear end of the outer shield 48 is threaded, as seen at 56, for engagement with the storage portion 50. The storage portion 50 is formed with a generally cylindrical side wall 58 having an open end 60 and a closed end 62. Adjacent the open end 60, the side wall 58 is bifurcated, having an outer wall portion 64 and an inner wall portion 66. The outer wall portion may be internally threaded for engagement with the threaded portion 56 of the outer shield 48. Alternatively, an internally threaded sleeve 71 may be slideably carried by the side wall 58 of the storage portion 50 and may engage the threaded portion 56 of the outer shield 48 to releasably secure the storage portion 50 to the outer shield 48. The inner wall portion 66 serves, when the storage portion 50 is threaded onto the outer shield 48, to bear against the apertured plate 21 of the tool portion 46 to urge the tool portion 46 forward and cause the opening 52 of the outer shield 48 to bear against the flexible outer tip 32 of the tool portion 46 to clamp the outer tip 32 against a strand of flossing material, not shown, to prevent moisture from entering the interior of the tool portion 46 through bore 34 of the flexible outer tip 32. The closed end 62 of the storage portion 50 has a stud 68 formed on the inner surface to receive one end of a spool, not shown, of dental flossing material, similar to the spool 16 of FIG. 1. The opposite end of the spool is received by stud 70 projecting from the apertured plate 21.

The use of the dental flossing tool 44 of FIG. 2 is substantially identical to that of the dental flossing tool 10 of FIG. 1. A spool, not shown, of dental flossing material is inserted into the storage portion 50 so that one end of the spool is seated on the stud 68 of the storage portion 50 and the other end of the spool is seated on stud 70 on the rear end of the tool portion 46. Thus, the storage portion 50 serves as an internal storage area for the spool of dental flossing material. A strand, not shown, of dental flossing material from the spool is then threaded through the tool portion 46 until the strand projects out of the bore 34 of the flexible outer tip 32 of the tool portion 46, in the same manner as described above with respect to threading the strand 20 of flossing material from the spool 16 through the dental flossing tool 10 of FIG. 1 until the strand 20 projects from bore 34 of the flexible outer tip 32 of the dental flossing tool 10 of FIG. 1. To cause the flexible outer tip 32 of the dental flossing tool 44 of FIG. 2 to clamp against the strand, not shown, of flossing material, the outer shield 48 is threaded further into an internally threaded slip ring 49, which is slideably mounted on the outer wall portion 64 of the storage portion 50, causing the inner wall portion 66 and closed end 62, acting through the spool of flossing material, not shown, to urge the tool portion 46 forward against the outer shield 48 and causing opening 52 of the outer shield 48 to bear against the flexible outer tip 32. To release the clamping action, the outer shield 48 is merely threaded outwardly from the outer wall portion 64 of the storage portion 50, releasing the forward pressure against the tool portion 46 and, hence, relaxing the pressure of opening 52 of the outer shield 48 against the flexible outer tip 32 of the tool portion 46.

If desired, the inner wall portion 66 of the storage portion 50 may be omitted. When this is done, and the storage portion 50 is threaded onto the outer shield 48, the closed end 62 of the storage portion 50 will bear against the rear end of the spool, causing the spool to bear against the apertured plate 21 of the tool portion 46 to urge the tool portion 46 forward so that the flexible outer tip 32 will be compressed by the opening 52 of the outer shield 48. In addition, numerous other variations and modifications can, obviously, be made without departing from the spirit of the present invention. Therefore, it should be clearly understood that the forms of the present invention described above and shown in the accompanying drawing are illustrative only and are not intended to limit the scope of the present invention.

What is claimed is:

1. A dental flossing tool comprising:
   a tool having a handle and an elongated tip formed of rigid material having:
   a storage area for retaining a quantity of dental flossing material,
   sealing means located adjacent one end of said tip, means adjacent said tip for clamping said sealing means to prevent moisture from entering said tool, and
   means for controlling passage of a strand of dental flossing material through the interior of said tool to project out said tip adjacent said sealing means.

2. The dental flossing tool of claim 1 wherein:
   said sealing means has an axial bore extending therethrough to facilitate passage of said strand of flossing material therethrough.

3. A dental flossing tool comprising:
   a storage area internal of said tool for retaining a quantity of dental flossing material,
   a flexible member mounted adjacent one end of said tool serving to prevent moisture from entering said tool,
   means for controlling passage of a strand of dental flossing material through the interior of said tool to project out adjacent said flexible member,
   means movable into and out of a position to cause said flexible member to clamp against said strand of dental flossing material.

4. The dental flossing tool of claim 3 wherein:
   said movable means is an outer member having an opening formed adjacent said one end thereof of greater diameter than said strand of dental flossing material.

5. The dental flossing tool of claim 4 wherein:
   said outer member is threadedly mounted on said tool.

6. The dental flossing tool of claim 3 wherein:
   said flexible member and said means for controlling passage of said strand of dental flossing material through the interior of said tool comprise a first member,
   said storage area comprises a second member, and said movable means comprises a third member which encircles said second member and is threadedly connectable in a manner such that threading of said third member in a first direction with respect to said second member will cause said third member to bear against said flexible member while threading of said third member in the opposite direction will tend to release said third member from bearing against said flexible member.

7. The dental flossing tool of claim 6 wherein:
   said second member is generally cylindrical having a closed end and an open end,
   said open end having means formed thereon for threadedly engaging said third member.

8. The dental flossing tool of claim 7 further comprising:
   the wall of said second member adjacent said open end being bifurcated and having an inner wall portion formed to bear against the rear end of said first member when said third member is threadedly engaging said first member.

9. The dental flossing tool of claim 7 wherein:
   the closed end of said second member is formed with a stud projecting inwardly therefrom to receive one end of a spool of dental flossing material and the length of said second member is substantially equal to that of said spool so that when said third member is threaded in said first direction said closed end will cause the spool to bear against said first member to urge the flexible member of said first member against said third member to cause said flexible member to clamp a strand of dental flossing material projecting therethrough to prevent moisture from entering the interior of said first member.

10. The dental flossing tool of claim 3 wherein:
    said means movable into and out of a position to cause said flexible member to clamp against said strand of dental flossing material encircles said flexible member and said means controlling movement of the strand of flossing material and is formed with an opening in the wall of said movable means to provide access for manual actuation of said brake member.

11. The dental flossing tool of claim 3 wherein:
    said flexible member bears against said strand of dental flossing material and serves to retard withdrawal of said flossing material from within said tool.

12. A dental flossing tool comprising: p1 a storage area internal of said tool for retaining a quantity of dental flossing material,
    a flexible member mounted adjacent one end of said tool serving to prevent moisture from entering said tool,
    means for controlling passage of a strand of dental flossing material through the interior of said tool to project out adjacent said flexible member including a manually-actuable brake member located internally of said tool,
    an opening formed in a wall of said tool adjacent said brake member, and
    a flexible, water-impervious membrane mounted to seal the opening in said wall to prevent moisture from entering the interior of said tool through said opening.

* * * * *